(12) United States Patent
Dai

(10) Patent No.: US 9,200,033 B2
(45) Date of Patent: Dec. 1, 2015

(54) ENZYME-DEGRADABLE POLYMER AND APPLICATION THEREOF

(75) Inventor: Lijun Dai, Jiangsu (CN)

(73) Assignee: KAREBAY BIOCHEM INC., Rochester, NY (US)

( * ) Notice: Subject to any disclaimer, the term of this patent is extended or adjusted under 35 U.S.C. 154(b) by 87 days.

(21) Appl. No.: 14/119,382

(22) PCT Filed: May 24, 2011

(86) PCT No.: PCT/CN2011/074593
§ 371 (c)(1),
(2), (4) Date: Apr. 30, 2014

(87) PCT Pub. No.: WO2012/159263
PCT Pub. Date: Nov. 29, 2012

(65) Prior Publication Data
US 2014/0243429 A1    Aug. 28, 2014

(51) Int. Cl.
| | |
|---|---|
| A61K 31/4353 | (2006.01) |
| A61K 31/437 | (2006.01) |
| A61K 38/55 | (2006.01) |
| A61K 38/03 | (2006.01) |
| A61K 47/48 | (2006.01) |
| C12Q 1/37 | (2006.01) |
| G01N 33/50 | (2006.01) |
| C07K 2/00 | (2006.01) |
| A61K 9/51 | (2006.01) |
| A61K 47/42 | (2006.01) |
| C12Q 1/34 | (2006.01) |

(52) U.S. Cl.
CPC ............... *C07K 2/00* (2013.01); *A61K 9/5146* (2013.01); *A61K 47/42* (2013.01); *C12Q 1/34* (2013.01)

(58) Field of Classification Search
None
See application file for complete search history.

(56) References Cited

U.S. PATENT DOCUMENTS 5,567,440 A * 10/1996 Hubbell et al. ............... 424/484

FOREIGN PATENT DOCUMENTS

| CN | 1634591 A | 7/2005 |
|---|---|---|
| CN | 1683014 A | 10/2005 |
| WO | 95/09883 A1 | 4/1995 |
| WO | 03/104424 A2 | 12/2003 |
| WO | 2007/082331 A1 | 7/2007 |

OTHER PUBLICATIONS

Gray et al. 2000. Characterization of human HtrA2, a novel serine protease involved in the mammalian cellular stress response. European Journal of Biochemistry, vol. 267, pp. 5699-5710.*

Matayoshi, E.D. et al., Novel fluorogenic substrates for assaying retroviral proteases by resonance energy transfer. Science. Feb. 23, 1990, vol. 247, No. 4945, pp. 954-958.

Homer, Karen A. et al., Fluorometric Determination of Bacterial Protease Activity Using Fluoroscein Isothiocyanate-Labeled Proteins as Substrates. Analytical Biochemistry, 1990, vol. 191, pp. 133-1376.

International Search Report in International application No. PCT/CN2011/074593, mailed Mar. 8, 2012.

* cited by examiner

*Primary Examiner* — Debbie K Ware
*Assistant Examiner* — Kailash C Srivastava
(74) *Attorney, Agent, or Firm* — Weisun Rao; Greenberg Traurig, LLP

(57) ABSTRACT

The present invention belongs to the biomedicine field and specifically concerns an enzyme-degradable polymer and the application thereof. To solve the problem of low sensitivity of the existing assay reagents, the present invention provides an enzyme-degradable polymer and the related application of the polymer. The present invention also provides hydrogels, nano-particles, fluorescent dye-labeled enzyme substrates and kits (packages) for detection or activity-analysis of biological enzymes based on the enzyme-degradable polymer. The formula of the enzyme-degradable polymer is $P_1$-(aa)$_N$-(AA)$_n$-X X=[formula 1] wherein, (aa)$_N$ is a non-enzyme substrate domain, the N aa may be different (no correlation), and N is a non-negative integer; (AA)$_n$ is an enzyme substrate domain, the n AA may be different, and n is a non-negative integer; $P_1$ is a protecting group of α-amino or functional group; $P_2$ is a protecting group of α-amino; $P_3$ is —NH$_2$, a small molecule compound or a fragment of a polymer.

10 Claims, 2 Drawing Sheets

ENZYME-DEGRADABLE POLYMER AND APPLICATION THEREOF

CROSS-REFERENCE TO RELATED APPLICATION

This application is a national phase application and dams benefit, under 35 U.S.C. §371, of PCT/CN2011/074593, filed on May 24, 2011, the contents of which are incorporated herein by reference in their entirety.

TECHNICAL FIELD OF THE INVENTION

The present invention belongs to the biomedicine field and specifically concerns an enzyme-degradable polymer and application thereof.

BACKGROUND OF THE INVENTION enzyme-degradable polymer includes natural products and synthetic materials, which can be widely used in the fields of the drug release, clinical diagnosis, biological detection analysis and other fields.

General, the detection of the enzyme is realized through fluorescent, light or color changing, wherein, the most common method is coupling the enzyme substrate (short peptides or other small molecules substrate) with a single functional or bifunctional fluorescent dyes, luminescent substrate; first, the fluorescent dye, luminescent substrate is set to a latent state by electron-attracting effect, while these short peptides or other small molecules substrate are used as probe for detecting the enzyme. When the presence of the corresponding enzyme, the enzyme will cut off the part of its substrate first, to thereby remove the electron-withdrawing effect of the fluorescent dye, luminescent substrate. Finally, it is possible to directly detect the signal, such as light; or applying an external signal source, such as laser and later read-out the signal (fluorescence). This kind of enzyme detect substrate, an enzyme catalyze one time can only activate one molecule (monofunctional latent state fluorescent or luminescent labled materials) or ½ molecules (bifunctional latent state fluorescent or luminescent labled materials) of signal units. Therefore, this kind of enzyme detect substrate, the sensitivity of detection is lower.

Histone deacetylases (HDACs) are a class of proteases playing an important role in chromosome structure modification and regulation of gene expression. In cancer cells, the over-expression of HDACs results acetylation enhanced, thereby increasing the attraction between the DNA and histones by recovering histone positive charge, and to make the relaxed nucleosome become very close, this is not helpful for the specific gene expression, including several tumor suppressor gene. But, for the absence of the convenient tools for analysing HDAC, the screen of complex substance which can suppress HDAC is more difficult.

SUMMARY OF THE INVENTION

To overcome the defects above mentioned, the present invention provides an enzyme-degradable polymer and the use thereof, including the preparation of the hydrogels, the preparation of the nano particles, and the method for carrying medicine molecule, fluorescent dye-labeled enzyme substrates (enzyme detecting reagent) used for detecting the activity and concentration of enzyme based on the enzyme-degradable polymer. The hydrogels and nano particles provided by this invention are used for drug release, in vivo imaging, clinical diagnosis; the fluorescent dye-labeled enzyme substrate, and the kits (packages) for detection or activity-analysis of biological enzyme of this invention are used for the detection and analysis of biological enzyme, and the sensitivity of detection is more higher.

To reach the above target, the present invention apply the technical projects as follows:

Project 1. An enzyme-degradable polymer, wherein, the formula of the said polymer is $P_1\text{-}(aa)_N\text{-}(AA)_n\text{-}X$,

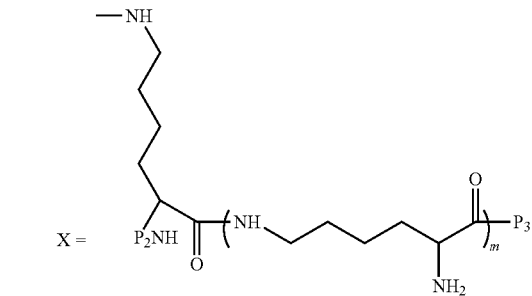

wherein, $(aa)_N$ is a non-enzyme substrate domain, the N aa may be different (no correlation), and N is a non-negative integer; $(AA)_n$ is an enzyme substrate domain, the n AA may be different, and n is a non-negative integer; $P_1$ is a protecting group of α-amino or functional group; $P_2$ is a protecting group of α-amino; $P_3$ is —$NH_2$, a small molecule compound or a fragment of a polymer.

Project 2. An enzyme-degradable polymer according to the project 1, wherein, aa in the $(aa)_N$ is an amino acid or a derivative thereof; AA in the $(AA)_n$ is an amino acid or a derivative thereof; the said $P_1$ is α-amino protecting group, including t-butyloxycarbonyl, acetyl, hexanoyl, octanoyl, or benzyloxycarbonyl; $P_2$ is t-butyloxycarbonyl, acetyl, hexanoyl, octanoyl, benzyloxycarbonyl or H.

Project 3. An enzyme-degradable polymer according to the project 2, wherein, the said polymer is cleaved by the I-type enzyme at the C-terminal of $(AA)_n$, to expose the ε-amine of the subsequent Polylysine; the Polylysine fragment is then further cleaved by the II-type enzyme, such as Trypsin, or other enzyme which can cleave the C-terminal of the unprotect Lysine, and degrade into single lysine. The mechanism is as follows:

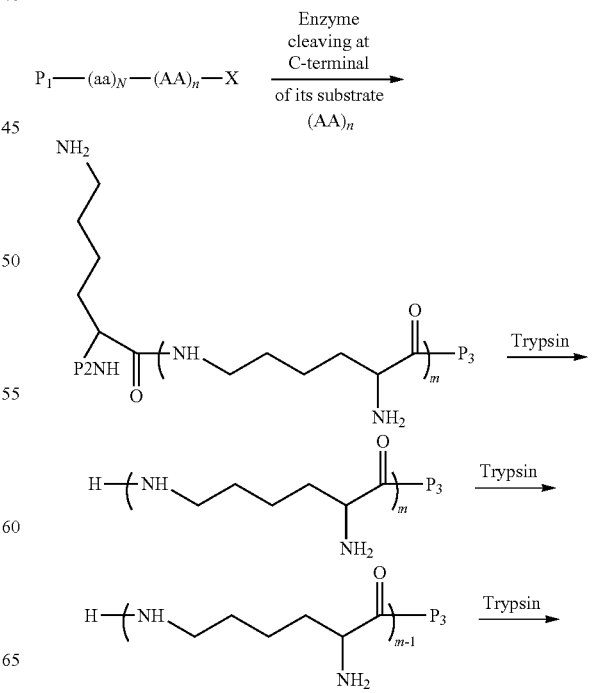

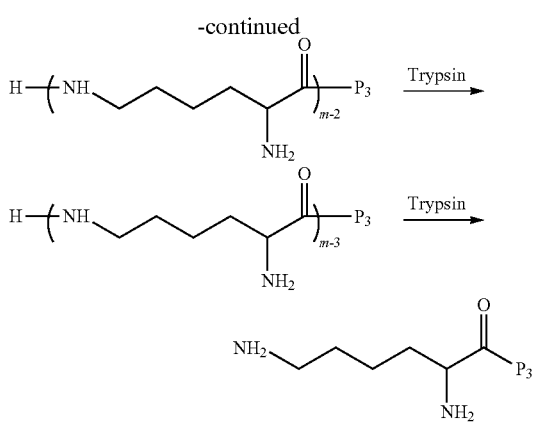

Project 4. An enzyme-degradable polymer according to the project 3, wherein, the said $P_1$-$(AA)_n$-X is I-type enzyme substrate, the said I-type enzyme comprising: a cysteine-containing aspartic acid protein hydrolase family (caspase family of proteases: caspase-1, 2, 3, 6, 7, 8, 9, 10 and 12), dipeptidyl peptidase4 (DPPIV), calpain, chymotrypsin, serine protease, cathepsin (Cathepsins B, K and L), granzyme B, SARS protease, kallikrein, thrombin, aminopeptidase, serine aminopeptidase, tryptase, histone deacetylases (HDACs), deacetylases (sirtuins);

I-type enzyme includes, but does not limited to the enzyme listed in the Table 1; wherein, the said I-type enzyme does not include trypsin; the substrates of the I-type enzyme, P1-$(AA)_n$-X includes but does not limited to the substrates corresponding to the enzyme listed in the Table 1.

| substrate P1-$(AA)_n$-X | enzyme | substrate P1-$(AA)_n$-X | enzyme |
| --- | --- | --- | --- |
| Z-DEVD-X | caspases-3 and-7 | Z-IEPD-X | granzyme B |
| Z-LETD-X | caspase-8 | Z-IETD-X | granzyme B and caspase-6 |
| GP-X | dipeptidyl peptidase 4(DPPIV) | Z-TSAVLQ-X | SARS protease |
| Z-LEHD-X | caspase-9 | Z-VNSTLQ-X | SARS protease |
| Suc-LLVY-X | calpain-and chymotrypsin-like activities of proteasome | Z-FR-X | cathepsins B/L |
| Z-LRR-X | trypsin-like activity of proteasome | Boc-VPR-X | kallikrein or thrombin |
| Z-nLPnLD-X | caspase-like activity of proteasome | Z-GGR-X | thrombin |
| Z-QEVY | calpain and proteasome chymotrypsin-like activity | Z-LR-X | Cathepsin K |
| VP-X | dipeptidyl peptidase 4(DPPIV) | Z-AAF-X | aminopeptidase |
| Z-VDVAD-X | caspase-2 | Suc-AAPF-X | serine aminopeptidase |
| Z-VEID-X | caspase-6 | Z-PRNK-X | tryptase |
| Z-ATAD-X | caspase-12 | Z-RR-X | Cathepsin B |
| Z-VAD-X | All Caspase | Z-YVAD-X | caspase-1 |
| Z-AEVD-X | caspase-10 | Z-PHE-X | Serine Protease |
| Z-LEU-X | Serine Protease | Z-LR-X | Cathepsin K |
| Z-FR-X | Cathepsin L | Ac-X | HDACs, Sirtuins |

Project 5. An enzyme-degradable polymer according to the project 1, wherein, the structure of the said polymer is as following:

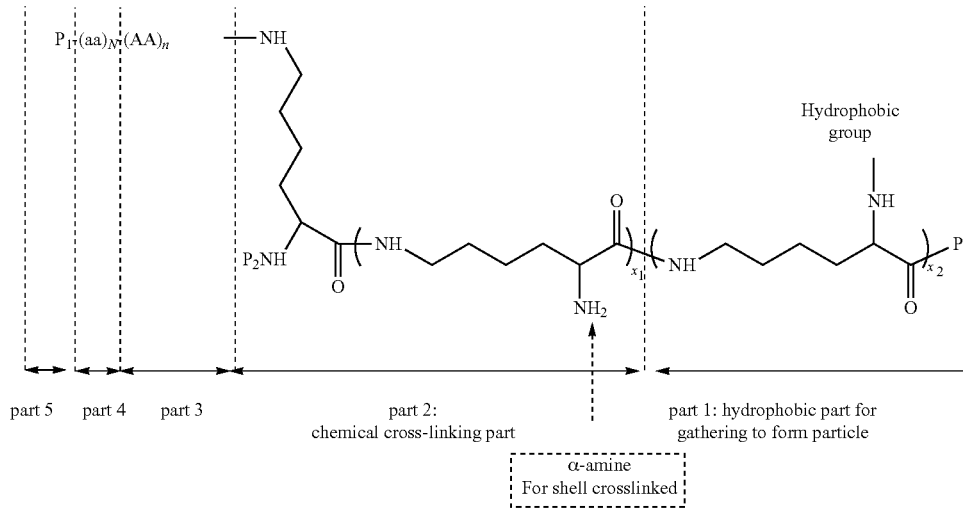

wherein,

Part 1: hydrophobic part for gathering to form particle, synthesized by α-amine of the Lysine, and cholesterol, lecithin, and so on, the biocompatible hydrophobic material, through covalent bond; wherein, $X_2$ is a positive integer, $P_3$ is —$NH_2$, the other small molecular compound or a polymer fragment;

Part 2: chemical crosslinking part, formed by the reaction of the α-amine of the Lysine and the difunctional or polyfunctional cross-linking agent, making the nana particles steady, wherein, $X_1$ is a positive integer, $P_2$ and n are defined as that in the project 1;

Part 3: the enzyme substrate part, the suitable enzyme can cleave the substrate at its C-terminal;

Part 4: hydrophilic part, including hydrophilic polymer, protein and/or peptide or hybrid, such as PEG, this part increase the ability of the water-soluble and can avoid the nano particles formed by the polymer induce an immune response when cycle in biological system;

Part 5: the surface functional group part, carrying functional group which may be further chemically modified, such as —COOH/$NH_2$—, and so on, and these functional groups can be further used for chemical coupling target fragment (antibody or a fragment thereof, biological ligands, etc.) or other biological/chemical fragment.

Project 6. An enzyme-degradable polymer according to the project 5, wherein,

Part 1: hydrophobic part for gathering to form particle, synthesized by α-amine of the Lysine and Lipoic acid through covalent bond; $X_2$=10, $P_3$=$NH_2$;

Part 2: chemical crosslinking part is formed by the reaction of the NHS-$PEG_{5000}$-NHS and the α-amine of Lysine, wherein, $X_1$=10;

Part 3: the enzyme substrate part, $(AA)_n$=DEVD (the substrate of Caspase 3/7), $P_2$=Ac;

Part 4: hydrophilic part, $(aa)_N$ is $PEG_{5000}$;

Part 5: the surface functional group part, is —$NH_2$.

Project 7. A hydrogel, wherein, the said enzyme-degradable polymer according to one of the projects 1 to 4 polymerizes to form the hydrogel. The said enzyme-degradable polymer react with the difunctional or polyfunctional cross-linking agent through the α-amine of the PolyLysine to form the hydrogel.

Project 8. A hydrogel, wherein, the said hydrogel comprise the said enzyme-degradable polymer according to one of the projects 1 to 4, the said enzyme-degradable polymer react with the other polymers (such as gelatin) by cross-linking agent to form the hydrogel.

Project 9. A nano particle, wherein, the said nano particle is polymerized by the said enzyme-degradable polymer according to the project 5 or project 6, the said hydrophobic part is in the interior of the nano particle, the said surface functional group part and the hydrophilic part are on the surface of the nano particle.

Project 10. A use of the nano particle according to the project 9, wherein, the said nano particle is used for drug carriers, drug release, in vivo imaging, clinical diagnosis.

Project 11. A fluorescent dye-labeled enzyme substrate, its formula is $P_1$-$(aa)_N$-$(AA)_n$-X,

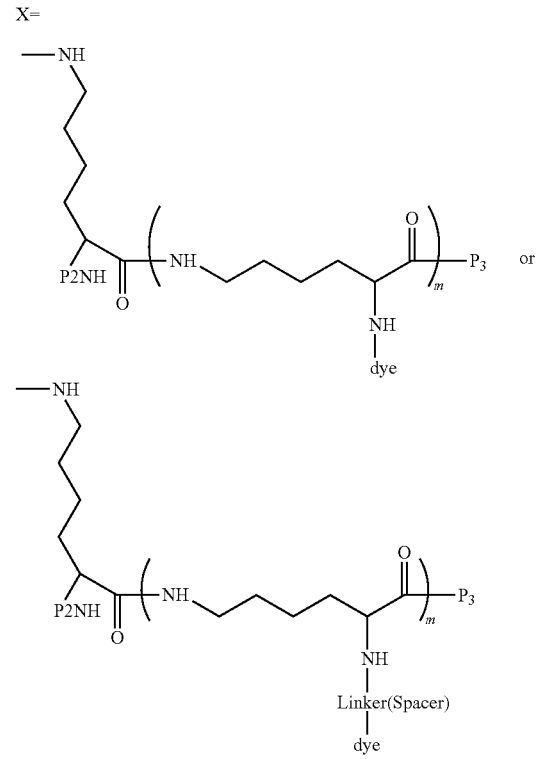

wherein, $(aa)_N$ is a non-enzyme substrate domain, the aa is an amino acid or a derivative thereof, the N aa may be different (no correlation), and N is a non-negative integer;

$(AA)_n$ is an enzyme substrate domain, the AA is an amino acid or a derivative thereof, the n AA may be different, and n is a non-negative integer;

$P_1$ and $P_2$ are protecting group of α-amino, including t-butyloxycarbonyl, acetyl, hexanoyl, octanoyl, or benzyloxycarbonyl; $P_2$ may be fluorescent dye too, $P_3$ is —$NH_2$, a small molecule or a fragment of large molecule;

The dye molecule is Self-quenching dye, m is an integer equal to or greater than 1.

Project 12. A fluorescent dye-labeled enzyme substrate according to the project 11, wherein, the fluorescence of the dye molecules in the fluorescent-labeled enzyme substrate is quenched by the dye molecules near by, when the fluorescent-labeled enzyme substrate is cleaved by the I-type enzyme and II-type enzyme according to the project 3, and degrades to single molecule of dye-α-Lysine-OH or dye-linker-(α)-Lysine-OH, the fluorescence intensity can be enhanced and detected.

Project 13. A method of the fluorescent dye-labeled enzyme substrate according to the project 11 used for detecting the activity or concentration of the I-type enzyme in the claim 3, as described below:

The fluorescent-labeled enzyme substrate dissolved in trace organic solvent, such as DMSO, is added in the sample containing I-type enzyme to be detected according to the project 3, and mixed for some time; further add excess II-type enzyme according to the project 3, and mixed for some time, then measure the fluorescence intensity; at the same time, the fluorescent-labeled enzyme substrate dissolved in trace organic solvent, such as DMSO, is added in the blank sample without I-type enzyme to be detected, and mixed for some time; further add the same excess II-type enzyme, and mixed for some time, then measure the fluorescence intensity.

Project 14. A fluorescent dye-labeled enzyme substrate according to the project 12, wherein, the dye molecules is self-quenching dye.

Project 15. A fluorescent dye-labeled enzyme substrate according to the project 14, wherein, the self-quenching dye molecule comprises Cy7, Cy5.5, Cy5, Cy3.

Project 16. A kits (packages) for detection or activity-analysis of biological enzymes, wherein, the kits (packages) comprise the said fluorescent-labeled enzyme substrate according to the project 11, 12, 14 or 15, and the corresponding enzyme, an appropriate buffer.

The enzyme detection reagent of the present invention, deprotect the ϵ-amino on the lysin which close to the C-terminal of the enzyme substrate in the polylysine, under the action of the C-terminal cutting enzyme to be detected first, then, the polylysine, under the cleaving of the excess enzyme, such as Trypsin, added sequentially, release the lysine monomers carrying a single dye molecule, to relieve the self-quencher and release a large number of fluorescent molecules. Compared with the prior enzyme detect substrate, an enzyme catalyze one time can only activate one molecule or ½ molecule of signal units, the present invention greatly improve the efficiency of the enzyme catalyze or induce the detection signal.

Compared with the prior art, the enzyme-degradable polymer, hydrogels, nano-particles provided by the present invention have good biocompatibility, can be used for drug release, in vivo imaging, clinical diagnosis; the fluorescent dye-labeled enzyme substrate provided by the present invention, Biology enzyme assays or activity assay kit (package) can be used for the detection and analysis of the enzyme, and the sensitivity is more higher.

DETAILED DESCRIPTION OF PREFERRED EMBODIMENTS

Example 1

Figure 1:
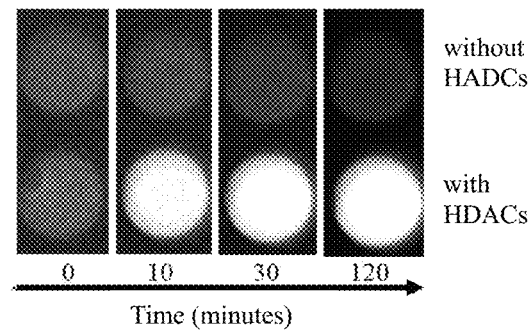
FIG. 1 shows the results of the fluorescent dye-labeled enzyme substrate provided by the present invention detect HDACs.

Synthesis of the enzyme-degradable polymer provided by the present invention.

Polypeptide is synthetized by the 433A automatic solid-phase synthesis instrument produced by the Applied Biosystems, Inc, using solid phase polypeptide synthesis Fmoc method, the insoluble carrier resin use the Fmoc-Rink Amide TentaGel solid phase synthesis resin produced by AnaSpec, an USA Company, HBTU/HOBt (0.45 M in DMF)/DIPEA (2 M DIPEA in NMP) or HATU/DIPEA act as an activator, piperidine act as a deprotection agent. 10 times the resin (0.1 mmol), the appropriately protected amino acid (1 mmol) is contained in a small plastic bottle (cartridge). The NMP is used as a solvent in the coupling process, and dichloromethane (DCM) is used to wash the solid phase resin (before and after the coupling reaction).

The Process of the Solid Phase Synthesis:

(1) Add the first amino acid to the Fmoc-Rink Amide TentaGel resin. First, remove the Fmoc group on the TentaGel resin (0.1 mmol) with 20% piperidine DMF solution, and then, wash the resin with DMF/DCM. Then, add 1 mmol Boc-Lys (Fmoc)-OH, 1 mmol DICI, and 1 mmol HOBT DMF solution into the resin solution, react at room temperature for 2-5 hours, wash the resin successively with DMF/DCM/Methanol/DCM, add the benzoic anhydride 3 mmol, and react for 30 minutes, then, wash the resin again as above mentioned.

(2) Place the following amino acids on the amino acid orbit of the ABI 433A automatic synthesizer with the following order:

I-type enzyme: HDACs, Sirtuins (histone deacetylase, sirtuin)

(N-terminal) Ac-Lys (Ac)—OH, [Boc-Lys(Fmoc)-OH] m-1 (C-terminal)

Remarks: [Boc-Lys (Fmoc)-OH]m-1 refers to the total of m-1 consecutive placed Boc-Lys (Fmoc)-OH cartridge, the other similar expression have the same meaning I-type enzyme: Caspase 3/Caspase 7

(N-terminal) Ac-Asp (OtBu)-OH, Fmoc-Glu (OtBu)-OH, Fmoc-Val-OH, Fmoc-Asp (OtBu)-OH, [Ac-Lys (Fmoc)-OH], [Boc-Lys (Fmoc)-OH]m-1 (C-terminal)

I-type enzyme: Caspase 8

(N-terminal) Z-Leu-OH, Fmoc-Glu (OtBu)-OH, Fmoc-Tyr (OtBu)-OH, Fmoc-Asp (OtBu)-OH, [Ac-Lys (Fmoc)-OH], [Boc-Lys (Fmoc)-OH]m-1 (C-terminal)

Using the following procedure to cut the polypeptides off the resin: per 100 mg resin carrying polypeptide, add 1-1.5 ml of a mixture of the following proportions: (TFA:water:Tis=95:2.5:2.5). The solution of the resin mixture is then shaking for 0.5-3 hours at room temperature. Subsequently, the mixture solution is filtered to remove the resin, and then added into the ice-cold diethyl ether dropwise to precipitate out, through repeated centrifugation and washing, and finally, the polypeptide is dried under nitrogen protection.

The polypeptide is dissolved in 1% TFA (trifluoroacetic acid) and acetonitrile aqueous solution, and then is injected into a C18 column to proceed the reverse HPLC analysis. The HPLC peak materials are collected and analyzed by mass spectrometry.

Remarks:
TIS: Triisopropylsilane
TFA: Trifluoroacetic acid
HOBt: 1-Hydroxylformamide
DMF: N,N-Dimethylformamide
DCM: Dicholoromethane
DIPEA (DIEA): N,N-diisopropyl-ethylamine
NMP: N-methylpyrrolidone
HATU: 2-(7-Aza-1H-benzotriazole-1-yl)-1,1,3,3-tetramethyluronium Hexafluorophosphate
HBTU: 2-(1H-Benzotriazole-1-yl)-1,1,3,3-tetramethyluroniumHexafluorophosphate
DICI: N,N'-Diisopropylcarbodiimide Example 2

The synthesis method of the hydrogel according to project 7 provided by the present invention.

Hydrogel synthesis example: Polymer is: Ac-DEVD-X, $P_2Ac$, $P_3=NH_2$, m=10, dissolved the polymer 1 mmol in 1-5 ml of DMF solution, then add 2-5 mmol glutaraldehyde or NHS-$(PEG)_{2000}$-NHS or NHS-$(PEG)_{5000}$-NHS and 6 mmol DIPEA, and the mixture is stirred for 1-24 hours. Extract most of the solvent by vacuum, then, add 1×PBS buffer which is 10 times the residual organic solvent, then the solution is transferred to dialysis Bag (the highest permeation molecular weight is 5000), the solution is stirred overnight in 1×PBS buffer to remove residual organic solution. The hydrogel obtained is frozen storage after low-temperature drying.

Example 3

The synthesis methods of hydrogel according to the project 8 provided by the present invention The hydrogel synthesis example: polymer is: Ac-DEVD-X, $P_2$=Ac, $P_3$=$NH_2$, m=10, and gelatin.

D, E, V, D in the segment DEVD are the single-letter codes for the amino acids aspartic acid, glutamic acid, valine, and aspartic acid, respectively; and Ac stands for acetyl.

1 mmol polymer and 1 mmol gelatin (number average molecular weight is 2000) is dissolved in 2-5 mL of DMF solution, then, add 3-10 mmol of glutaraldehyde or NHS-$(PEG)_{2000}$-NHS or NHS-$(PEG)_{5000}$-NHS and 6 mmol DIPEA, and the mixture is stirred for 1-24 hours. Get rid of most of the solvent by vacuum, then, add 1×PBS buffer which is 10 times the residual organic solvent, then the solution is transferred to a dialysis Bag (the highest permeation molecular weight is 5000), the solution is stirred overnight in 1×PBS buffer to remove residual organic solution. The hydrogel obtained is frozen storage after low-temperature drying.

Example 4

Synthesis method of the enzyme-degradable polymer according to the project 6 provided by the present invention.

The Process of the Solid Phase Synthesis:

(1) Add the first amino acid to the Fmoc-Rink Amide TentaGel resin. First, remove the Fmoc group on the TentaGel resin (0.1 mmol) with 20% piperidine DMF solution, and then, wash the resin with DMF/DCM. Then, add 1 mmol Dde-Lys(Fmoc)-OH (produced by the BaChem, USA), 1 mmol DICI and 1 mmol HOBT DMF solution into the resin solution, react at room temperature for 2-5 hours, wash the resin successively with DMF DCM/Methanol/DCM, add the benzoic anhydride 3 mmol into the resin, and react for 30 minutes, then, wash the resin again as above mentioned.

(2) Place the following amino acids (each amino acid is 1 mmol) on the amino acid orbit of the ABI 433A automatic synthesizer with the following order:

(N-terminal) Fmoc-$PEG_{5000}$-NHS, Boc-Asp(OtBu)-OH, Fmoc-Glu(OtBu)-OH, Fmoc-Val-OH, Fmoc-Asp(OtBu)-OH, [Ac-Lys(Fmoc)-OH], [Boc-Lys(Fmoc)-OH]$_{10}$, [Dde-Lys(Fmoc)-OH]$_9$ (C-terminal)

Remarks: [Boc-Lys (Fmoc)-OH]$_{10}$ refers to the 10 Boc-Lys (Fmoc)-OH cartridges is consecutive placed, each of the 10 consecutive placed Boc-Lys (Fmoc)-OH cartridges is 1 mmol, the other similar expression have the same meaning.

After the solid phase automatic synthesis finished, treat the resin with 2% Hydrazine solution to deprotect the Dde group in the Dde-Lys(Fmoc)-OH.

Mix the 30 mmol lipoic acid and 30 mmol HATU, 60 mmol DIPEA (DMF solution) for 5 minutes, then add the mixture into the above resin, after the reaction for 1 hour, wash the resin successively with DMF/DCM.

Using the following procedure to cut the polymer off the resin: per 100 mg resin carrying polypeptide, add 1 ml mixture of the following proportions: (TFA:water:Tis=95:2.5:2.5). The solution of the resin mixture is then shaking for 0.5-3 hours at room temperature. Subsequently, the mixture solution is filtered to remove the resin, and then added into the ice-cold diethyl ether dropwise to precipitate out, through repeated centrifugation and washing, and finally, the polypeptide is dried under nitrogen protection.

The polymer is dissolved in 1% TFA (trifluoroacetic acid) and acetonitrile aqueous solution, and then is injected into a C18 column to proceed the reverse HPLC analysis. The HPLC peak materials are collected and analyzed by mass spectrometry.

Example 5

The nano particles according to the project 9 of the present invention is used as pharmaceutical carrier.

Dissolve 10 mg polymer obtained in Example 4 and 0.5 mg adriamycin (Doxorubicin) in 1-10 ml acetone or tetrahydrofuran, and the solution is added dropwise into 10-100 ml deionized water which maintain ultrasonic vibration. After the dropwise addition finished, 2 mg NHS-$PEG_{2000}$-NHS is added to the water, and subsequently stirred for 2 hours, and then the solution is transferred to a dialysis Bag (the highest permeation molecular weight is 10,000), the solution is stirred overnight in 1×PBS buffer. Finally, the nano particles obtained is stored at 2-8° C.

Example 6

The synthetic method of the fluorescent dye-labeled enzyme substrate according to the project 11 of the present invention, wherein N=0; n=0; m=10, dye=Cy7, does not have the Linker (spacer); $P_3$=$NH_2$; $P_2$=Ac; $P_1$=Ac. This is HDACs substrate.

The Process of the Solid Phase Synthesis:

(1) Add the first amino acid to the Fmoc-Rink Amide TentaGel resin. First, remove the Fmoc group on the TentaGel resin (0.1 mmol) with 20% piperidine DMF solution, and then, wash the resin with DMF/DCM. Then, add 1 mmol Dde-Lys(Fmoc)-OH (produced by the BaChem Company, USA), 1 mmol DICI and 1 mmol HOBT DMF solution into the resin solution, react for 2-5 hours at room temperature, wash the resin successively with DMF/DCM/Methanol/DCM, add the benzoic anhydride 3 mmol into the resin, and react for 30 minutes, then, wash the resin again as above mentioned.

(2) Place the following amino acids (each amino acid is 1 mmol) on the amino acid orbit of the ABI 433A automatic synthesizer with the following order:

(N-terminal) Ac-Lys(Ac)—OH, [Dde-Lys(Fmoc)-OH]$_{10}$ (C-terminal)

After the solid phase automatic synthesis finished, treat the resin with 2% Hydrazine solution to deprotect the Dde group in the Dde-Lys(Fmoc)-OH, Add the 30 mmol Cy7-NHS (produced by the GE HealthcareCompany), react for 1 hour, then wash the resin successively with DMF/DCM.

Using the following procedure to cut the polymer off the resin: per 100 mg resin carrying polypeptide, add 1 ml mixture of the following proportions: (TFA:water:Tis=95:2.5:2.5). The solution of the resin mixture is then shaking for 2 hours at room temperature. Subsequently, the mixture solution is filtered to remove the resin, and then added dropwise into the ice-cold diethyl ether to precipitate out the polypeptide, through repeated centrifugation and washing, and finally, the polypeptide is dried under nitrogen protection.

The polymer is dissolved in 1% TFA (trifluoroacetic acid) and acetonitrile aqueous solution, and then is injected into a C18 column to proceed the reverse HPLC analysis. The HPLC peak materials are collected and analyzed by mass spectrometry.

Example 7

The application of the fluorescent dye-labeling enzyme substrate of the present invention
Detection of the HDACs.

The HDACs substrate obtained in Example 6 is formulated into 100 mM DMSO solution, and then the substrate is diluted to 100 μM with the HDAC analysis buffer, the substrate solution is added into two adjacent wells of a 96-Well Microplate (black, V-shaped bottom, 96-Well Microplate), each well contains 100 μL substrate. And then, add 1 μL (1 microliter) HeLa Cell Nuclear Extract into a well (sample well) (produced by the Biomol International company, U.S.A); add 1 μL deionized water into the control well. Shaking for 1 hour at room temperature, and then, add trypsin into the two wells at the same time, and immediately place the 96-Well Microplate in the KODAK vivo imaging instrument, the camera starts to record the sample well and the control wells. The results obtained are shown in FIG. 1. Obviously, the fluorescent dye-labeled enzyme substrate of the present invention has more higher sensitivity in the enzyme detection and analysis.

Example 8

Figure 3:
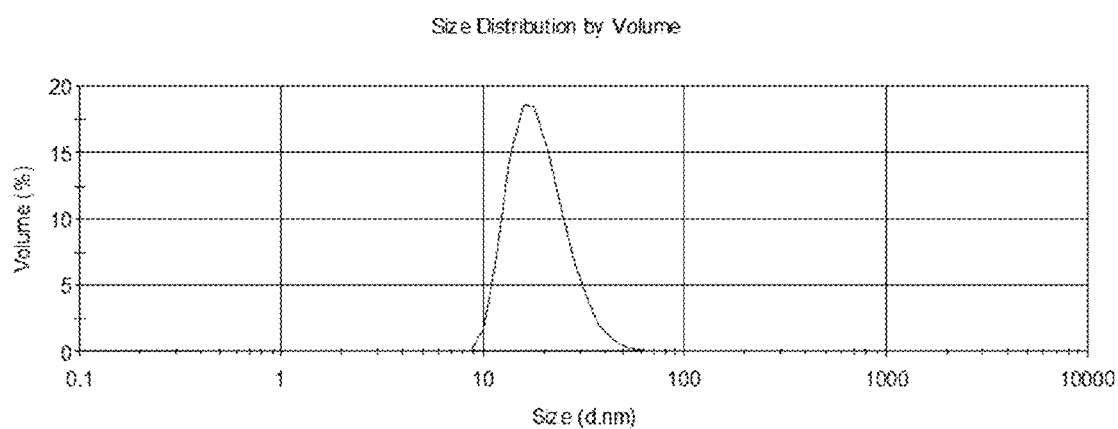
FIG. 3 shows the size distribution by volume of the nano particals provided by the present invention.

The synthetic method of the nano-particles of the present invention, as described below:

Dissolve the 10 mg polymer obtained in the Example 4 in 1-10 ml acetone or tetrahydrofuran, and the solution is then added dropwise into 10-100 ml deionized water which maintain ultrasonic vibration, after the dropwise addition finished, then add 2 mg NHS-PEG$_{2000}$-NHS into the water, after stirring for 2 hours, then transfer the solution into the dialysis Bag (the highest permeation molecular weight is 10,000), the solution is stirred overnight in 1×PBS buffer, Measure the particle size of the nano particles obtained with the Dynamic light scattering particle size analyzer produced by the Malvern company (DLS, polystyrene particles with known particle size are used as standard sample). The size distribution by volume of the nano particles is shown in FIG. 3.

Figure 2:
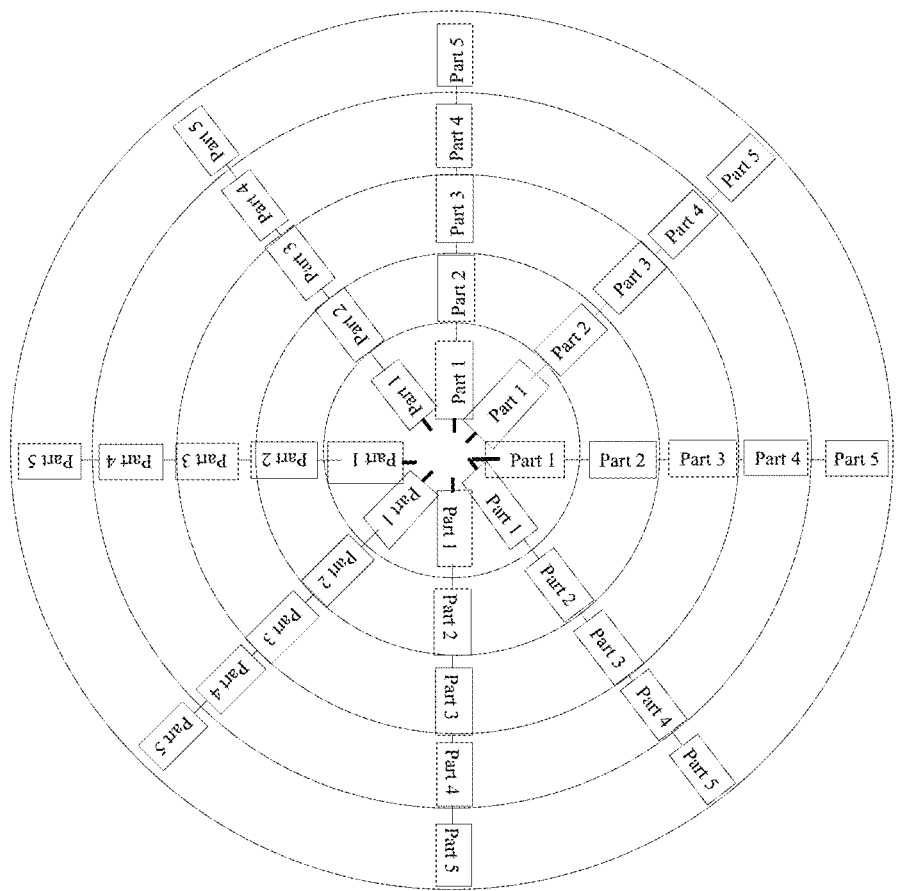
FIG. 2 is structural schematic view of the the structure of the nano particals provided by the present invention.

The structure of the nano particles is shown in FIG. 2.

The above described is the preferred embodiment of the present invention only, and not intended to limit the scope of protection of the present invention. All modifications and alterations made to the content of the present invention, are covered within the scope of the present invention.

I claim:

1. An enzyme-degradable polymer having the formula of $P_1$-(aa)$_N$-(AA)$_n$-X, wherein:

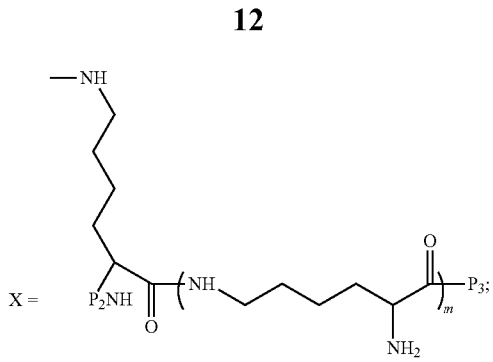

(aa)$_N$ is a non-enzyme substrate domain, aa in the (aa)$_N$ is an amino acid that can be the same or different from each other, and N is a non-negative integer;

(AA)$_n$ is an enzyme substrate domain, AA in the (AA)$_n$ is an amino acid that can be the same as or different from each other, and n is a non-negative integer;

$P_1$ is a protecting group of α-amino and is selected from the group consisting of t-butyloxycarbonyl, acetyl, hexanoyl, octanoyl, or benzyloxycarbonyl;

$P_2$ is selected from the group consisting of t-butyloxycarbonyl, acetyl, hexanoyl, octanoyl, benzyloxycarbonyl or H;

$P_3$ is —NH$_2$; and m is an integer equal to or greater than 1.

2. The enzyme-degradable polymer according to claim 1, wherein the polymer is cleaved by an I-type enzyme at the C-terminal of (AA)$_n$, to expose the ε-amine of a subsequent polylysine further cleaved by an II-type enzyme and degrades into single lysine; the I-type enzyme is selected from the group consisting of caspase-1, 2, 3, 6, 7, 8, 9, 10, 12, dipeptidyl peptidase4, calpain, chymotrypsin, serine protease, Cathepsin B, Cathepsin K, Cathepsin L, granzyme B, SARS protease, kallikrein, thrombin, aminopeptidase, serine aminopeptidase, tryptase, serine protease, histone deacetylase, and deacetylase; and the II-type enzyme is trypsin.

3. The enzyme-degradable polymer according to claim 2, wherein the $P_1$-(aa)$_N$-(AA)$_n$-X is an I-type enzyme substrate in which N is 0, and the I-type enzyme is deacetylase.

4. The enzyme-degradable polymer according to claim 2, wherein the $P_1$-(aa)$_N$-(AA)$_n$-X is an I-type enzyme substrate in which N is 0, and the substrate and the corresponding I-type enzyme which does not include trypsin are listed in pair below

| substrate P1-(aa)$_N$-(AA)$_n$-X | enzyme | substrate P1-(aa)$_N$-(AA)$_n$-X | enzyme |
|---|---|---|---|
| Z-DEVD-X | caspases-3 and-7 | Z-IEPD-X | granzyme B |
| Z-LETD-X | caspase-8 | Z-IETD-X | granzyme B and caspase-6 |
| GP-X | dipeptidyl peptidase 4(DPPIV) | Z-TSAVLQ-X | SARS protease |
| Z-LEHD-X | caspase-9 | Z-VNSTLQ-X | SARS protease |
| Suc-LLVY-X | calpain-and chymotrypsin-like activities of proteasome | Z-FR-X | cathepsins B/L |
| Z-LRR-X | trypsin-like activity of proteasome | Boc-VPR-X | kallikrein or thrombin |
| Z-nLPnLD-X | caspase-like activity of proteasome | Z-GGR-X | thrombin |
| Z-QEVY | calpain and proteasome chymotrypsin-like activity | Z-LR-X | Cathepsin K |
| VP-X | dipeptidyl peptidase 4(DPPIV) | Z-AAF-X | aminopeptidase |
| Z-VDVAD-X | caspase-2 | Suc-AAPF-X | serine aminopeptidase |
| Z-VEID-X | caspase-6 | Z-PRNK-X | tryptase |

-continued

| substrate P1-(aa)$_N$-(AA)$_n$-X | enzyme | substrate P1-(aa)$_N$-(AA)$_n$-X | enzyme |
|---|---|---|---|
| Z-ATAD-X | caspase-12 | Z-RR-X | Cathepsin B |
| Z-VAD-X | All Caspase | Z-YVAD-X | caspase-1 |
| Z-AEVD-X | caspase-10 | Z-PHE-X | Serine Protease |
| Z-LEU-X | Serine Protease | Z-LR-X | Cathepsin K |
| Z-FR-X | Cathepsin L | Ac-X | HDACs, Sirtuins. |

5. The enzyme-degradable polymer according to claim 1, wherein the structure of the polymer is as follows:

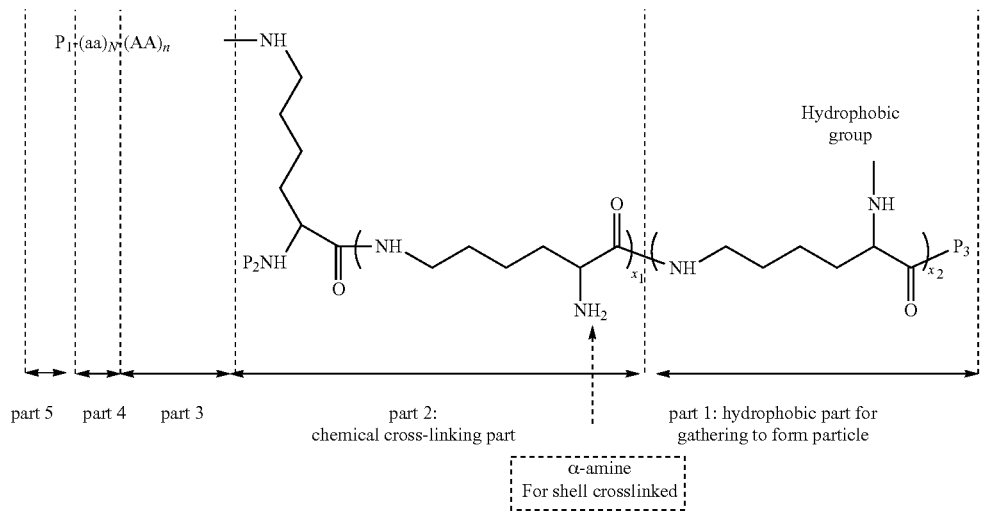

wherein,

Part 1 is synthesized by α-amine of the lysine and lipoic acid, wherein lysine and lipoic acid are connected by a covalent bond; $X_2$=10, $P_3$=NH$_2$;

Part 2 is formed by the reaction of the N-hydroxylsuccinimide (NHS)-PEG$_{5000}$-NHS and the α-amine of lysine; $X_1$=10, $P_2$=Ac;

in Part 3, (AA)$_n$=DEVD wherein D, E, and V stand for aspartic acid, glutamic acid, and valine respectively;

in Part 4, (aa)$_N$ is PEG$_{5000}$; and

Part 5 is —NH$_2$.

6. A nano particle having an interior part and a surface, wherein the nano particle is polymerized by the enzyme-degradable polymer according to claim 1, the interior of the nano particle is hydrophobic, the surface contains functional group part and is hydrophilic.

7. A fluorescent dye-labeled enzyme substrate of the formula P$_1$-(aa)$_N$-(AA)$_n$-X, wherein:

X=

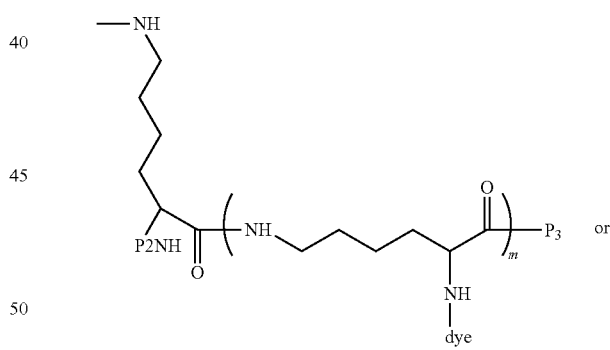

or

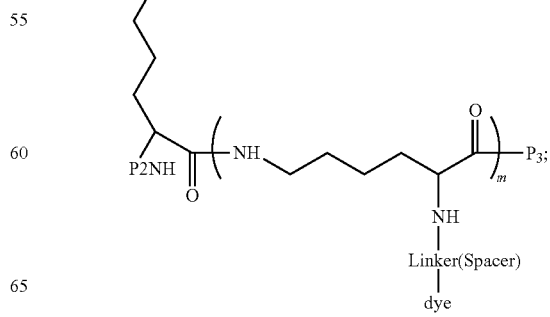

$(aa)_N$ is a non-enzyme substrate domain, aa in the $(aa)_N$ is an amino acid that can be the same or different from each other, and N is a non-negative integer;

$(AA)_n$ is an enzyme substrate domain, AA in the $(AA)_n$ is an amino acid that can be the same as or different from each other, and n is a non-negative integer;

m is an integer equal to or greater than 1;

$P_1$ is selected from the group consisting of t-butyloxycarbonyl, acetyl, hexanoyl, octanoyl, and benzyloxycarbonyl;

$P_2$ is selected from the group consisting of t-butyloxycarbonyl, acetyl, hexanoyl, octanoyl, benzyloxycarbonyl, and fluorescent dye;

$P_3$ is —$NH_2$; and the dye molecule is a self-quenching dye.

8. The fluorescent dye-labeled enzyme substrate according to claim 7, wherein the fluorescence of the dye is quenched by nearby dye molecules, when the fluorescent-labeled enzyme substrate is cleaved by an I-type enzyme and a II-type enzyme and degrades to single molecule of dye-α-Lysine or dye-linker-(α)-Lysine, wherein the fluorescence intensity can be detected; the I-type enzyme is selected from the group consisting of caspase-1, 2, 3, 6, 7, 8, 9, 10, 12, dipeptidyl peptidase4, calpain, chymotrypsin, serine protease, Cathepsin B, Cathepsin K, Cathepsin L, granzyme B, SARS protease, kallikrein, thrombin, aminopeptidase, serine aminopeptidase, tryptase, serine protease, histone deacetylase, and deacetylase; and the II-type enzyme is trypsin.

9. The fluorescent dye-labeled enzyme substrate according to claim 7, wherein the dye molecule is selected from the group consisting of Cy7, Cy5.5, Cy5, and Cy3.

10. A kit for detection of or determining activity of biological enzymes, comprising a fluorescent-labeled enzyme substrate according to claim 7, 8, or 9, a corresponding enzyme, and an appropriate buffer.

* * * * *